United States Patent [19]

Epperly et al.

[11] Patent Number: 5,215,652
[45] Date of Patent: Jun. 1, 1993

[54] METHOD FOR REGENERATING, REPLACING OR TREATING THE CATALYST IN A HYDROPROCESSING REACTOR

[75] Inventors: W. Robert Epperly, New Canaan; Barry N. Sprague, Bethlehem, both of Conn.; Danny T. Kelso, Houston, Tex.; Wayne E. Bowers, North Vassalboro, Me.

[73] Assignee: Platinum Plus, Inc., Rowayton, Conn.

[21] Appl. No.: 303,164

[22] Filed: Jan. 27, 1989

Related U.S. Application Data

[63] Continuation-in-part of Ser. No. 291,245, Dec. 28, 1988, abandoned, which is a continuation-in-part of Ser. No. 897,864, Aug. 19, 1986, Pat. No. 4,892,562, which is a continuation-in-part of Ser. No. 897,869, Aug. 19, 1986, Pat. No. 4,891,050, which is a continuation-in-part of Ser. No. 796,428, Nov. 8, 1985, abandoned, which is a continuation-in-part of Ser. No. 677,954, Dec. 4, 1984, abandoned, which is a continuation-in-part of Ser. No. 790,738, Oct. 24, 1985, abandoned.

[51] Int. Cl.$^5$ ............................................. C10G 35/08
[52] U.S. Cl. ........................... 208/140; 208/138; 208/139; 502/22; 502/31; 502/53
[58] Field of Search ............... 44/67, 68; 208/139, 208/138, 140; 585/419; 556/136, 137; 502/22, 31, 53

[56] References Cited

U.S. PATENT DOCUMENTS

| | | | |
|---|---|---|---|
| 2,086,775 | 7/1937 | Lyons et al. | 44/69 |
| 2,151,432 | 3/1939 | Lyons et al. | 44/69 |
| 2,875,223 | 2/1959 | Pedersen et al. | 260/439 |
| 3,369,035 | 2/1968 | Schultz | 252/49.7 |
| 3,397,214 | 8/1968 | Schultz | 252/49.7 |
| 4,207,078 | 6/1980 | Sweeney et al. | 44/68 |
| 4,224,235 | 9/1980 | Beisner et al. | 252/414 |
| 4,242,099 | 12/1980 | Malec | 44/53 |
| 4,295,816 | 10/1981 | Robinson | 123/1 A |
| 4,715,948 | 12/1987 | Sughrue et al. | 208/251 H |
| 4,741,820 | 5/1988 | Coughlin et al. | 208/139 |
| 4,787,969 | 11/1988 | Baird, Jr. | 208/139 |
| 4,795,549 | 1/1989 | Coughlin et al. | 208/139 |

OTHER PUBLICATIONS

Belluco, Organometallic and Coordination Chemistry of Platinum, Academic Press, NY, pp. 221, 222, 226, 232, 295–297, 441–442, 449, 454 & 455 (1974).
Deganello, Transition Metal Complexes of Cyclic Polyoefins, Academic Press, N.Y., pp. 97–100, 102, 277–278, 281–283, 288–291 (1979).
Dickson, Organometallic Chemistry of Rhodium and Iridium, Academic Press, N.Y., pp. 167–169, 178–180, 198–200, 220–226, 248, 258–260, 264, 271 & 277 (1983).
Maitlis, The Organic Chemistry of Palladium, Academic Press, N.Y., pp. 68, 70, 76, 77, 83, 93, 102, 103, 136, 158, 165, 202–204, 228, 242, 249, 257–258 (1971).
Chemical Abstracts 76 112565 p (1792).
Chemical Abstracts 76 11335 g (1792).
Chemical Abstracts 82 4403z (1975).
Chemical Abstracts 97 110175w (1982).
Chemical Abstracts 97 110181v (1982).

*Primary Examiner*—Margaret Medley
*Attorney, Agent, or Firm*—St. Onge Stewart Johnston & Reens

[57] ABSTRACT

The invention presented involves a method for regenerating, replacing or treating the catalyst in a hydroprocessing reactor, the method comprising admixing with the feedstock, recycle stream or hydrogen stream of the reactor an additive which comprises a nonionic, organometallic platinum group metal coordination composition which is a) resistant to breakdown under ambient temperatures; b) capable of breakdown at temperatures existing in the vicinity of the catalyst; and c) does not contain a disadvantageous amount of phosphorus, arsenic, sulfur, antimony or halides.

19 Claims, No Drawings

METHOD FOR REGENERATING, REPLACING OR TREATING THE CATALYST IN A HYDROPROCESSING REACTOR

RELATED APPLICATIONS

This application is a continuation-in-part of copending and commonly assigned U.S. Patent Application entitled "Method for Reducing Emissions From or Increasing the Utilizable Energy of Fuel for Powering Internal Combustion Engines", Ser. No. 291,245, filed on Dec. 28, 1988 now abandoned in the names of Epperly, Sprague, Kelso, and Bowers; which in turn is a continuation-in-part of copending and commonly assigned U.S. Patent Application entitled "Diesel Fuel Additives and Diesel Fuels Containing Soluble Platinum Group Metal Compounds and Use in Diesel Engines", Ser. No. 897,864, filed in the names of Bowers and Sprague on Aug. 19, 1986, now U.S. Pat. No. 4,892,562; and copending and commonly assigned U.S. Patent Application entitled "Gasoline Additives and Gasoline Containing Soluble Platinum Group Metal Compounds and Use in Internal Combustion Engines", Ser. No. 897,869, filed in the names of Bowers and Sprague on Aug. 19, 1986, now U.S. Pat. No. 4,891,051; each of which is a continuation-in-part of prior application Ser. No. 796/428, filed Nov. 8, 1985, now abandoned which in turn is a continuation-in-part of prior applications Ser. No. 677,954, filed Dec. 4, 1984, now abandoned and Ser. No. 790,738, filed Oct. 24, 1985, now abandon all by Bowers and Sprague, the inventors herein. The disclosures of each of these prior applications is hereby incorporated by reference herein.

TECHNICAL FIELD

The present invention relates to improving the performance of catalytically-mediated hydroprocessing reactors by providing a means for regeneration or redeposit of catalyst which has lost activity.

Hydroprocessing reactors perform a variety of reactions by passing a stream of hydrocarbons over a catalyst bed containing a catalyst material, preferably a platinum group metal catalyst, in the presence of hydrogen. One of the primary reactions performed in a hydroprocessing reactor is reforming, which is a process involving the production of, for instance, aromatics from low-octane petroleum fractions or other hydrocarbons by heat and pressure with a platinum group metal catalyst. The actual reforming process conditions depend on the particular reforming catalyst, the feedstock, the desired products, process design and the like. Reforming is used extensively in the petroleum and petroleum products industry to increase the octane quality of naphthas or straight-run gasolines. The chief reforming reactions are (1) dehydrogenation of cyclohexanes and dehydroisomerization of alkylcyclopentanes to yield aromatic hydrocarbons such as benzene, toluene, etc.; (2) dehydrocyclization of certain paraffins and olefins to yield aromatics; (3) dehydrogenation of paraffins to yield olefins; (4) isomerization, i.e., conversion of straight chain to branched chain structures such as octane to isooctane, of n-paraffins, substituted aromatics and alkylcycloparaffins; and (5) hydrocracking of paraffins to yield gas and inevitably coke (which can be deposited on the catalyst). A more detailed review of the reforming process including common process conditions, feedstocks, catalysts and catalyst bases and reactors used in such a process, is set out in U.S. Pat. No. 4,741,820 to Coughlin et al., U.S. Pat. No. 4,787,969 to Baird, Jr. and U.S. Pat. No. 4,795,549 to Coughlin et al., the disclosures of which are incorporated by reference herein in their entireties.

Often, through routine use or occasional operational upsets, the catalyst loses some or all of its activity. This can occur because of a build-up of coke or other materials on the catalyst, by contamination by a catalyst poison and/or by sintering (or agglomeration) of catalyst metal with resultant loss of surface area. Catalyst regeneration, replacement or treatment (which can be considered as differing from each other primarily by degree and as equivalent for the purposes of the present invention) is required to regain activity and associated process efficiency, which commonly requires shut-down and substantial disassembly of the reactor with attendant loss of time and significant negative financial implications.

What is desired, therefore, is a means to effectively replace or regenerate the catalyst on the catalyst bed without the need for disassembly and with reduced shut-down time of the hydroprocessing reactor.

1. Background Art

It has been known to supply platinum group metal compositions to internal combustion engines as fuel additives. For example, Lyons and McKone disclose in U.S. Pat. Nos. 2,086,775 and 2,151,432 adding from 0.001–0.085% (i.e. from 10 to 850 parts per million) of an organometallic compound or mixture to a base fuel such as gasoline, benzene, fuel oil, kerosene or blends to improve various aspects of engine performance.

A patent to Lyons and Dempsey, U.S. Pat. No. 2,460,780, relates principally to employing catalysts which are soluble in water or other "internal liquid coolants" such as alcohol or soluble glycols or aqueous solutions of these. While catalyst levels based on the weight of metal compounds as low as 0.001% are disclosed, it is stated that for immediate catalytic effect, the catalyst compounds for useful effect may be present at a level of at least 1% of the weight of the operating fuel charge.

Robinson, in U.S. Pat. No. 4,295,816, discloses an elaborate delivery system for introducing water soluble platinum group metal salts through the air intake of internal combustion engines to deliver platinum group metal catalysts to the combustion chamber at a level no greater than 9 milligram catalyst per kilogram of fuel. The equipment disclosed by Robinson, unfortunately, is far more complicated than would be desired and the water soluble salts employed e.g. halides, have disadvantages alone or when dissolved.

In German Offenlegungsschrift 2,500,683, Brantl discloses a wide variety of catalytic metals which may be added to hydrocarbon fuels to reduce nitrogen monoxide and oxidize carbon monoxide at the moment of combustion in internal combustion engines. Among the metals disclosed are metal complexes of the metals ruthenium, rhodium, palladium, osmium, iridium and platinum, with different ligands, which can be added to the fuel individually or as a mixture. For these platinum group metals, broad concentration ranges of from 0.347 to 3.123 grams per liter of fuel are suggested for the various compositions listed in the disclosure, with the range for particularly favorable results being from 0.868 to 1.735 grams per liter of fuel.

Although the art has identified platinum group metal compounds as superior catalysts for improving fuel efficiency and reducing noxious emissions, regeneration or replacement of the catalyst in a hydroprocessing reactor by the use of platinum group metal compositions as feedstock, recycle stream or hydrogen stream additives has not heretofore been suggested.

2. Disclosure of Invention

The present invention comprises a method for regenerating, replacing or treating the catalyst in a reforming reactor and involves the application of certain platinum group metal compounds to either the feedstock, the recycle stream or the hydrogen stream of the reactor. The compounds are preferably applied to the feedstock or recycle stream, most preferably in combination with a solvent for them which is also miscible in the feedstock or recycle stream, and are employed either continuously at very small but catalytically effective levels to provide from about 0.01 to about 10.0 parts of platinum group metal per 1 million parts of feedstock or recycle stream (ppm) to continuously regenerate the catalyst while maintaining the reactor in operation, or, most advantageously and more efficiently, intermittently at higher levels to provide from about 10 to about 10,000 parts of platinum group metal per 1 million parts of feedstock or recycle stream (ppm) to regenerate the catalyst on the catalyst bed as needed. Such an intermittent method of catalyst regeneration or redeposit can be expected to deposit about 0.002 to about 2.0 grams of platinum group metal on the catalyst bed per hour per 100 grams of catalyst.

The most preferred method of intermittent introduction of the additive is as a solution in a hydrocarbon solvent which is added to the feedstock or recycle stream and passed over the catalyst at a temperature below about 200° C., and preferably below about 100° C., to deposit the additive on the catalyst. After deposit of the desired amount of platinum group metal on the catalyst bed, the flow of liquid is stopped and the excess liquid is purged from the catalyst, for instance by hydrogen. The catalyst is then activated by heating the hydrogen stream to thereby heat the catalyst and drive off the adsorbed carrier solvent, leaving a catalytically active surface of platinum group metal. If necessary, the catalyst is subjected to burning, chlorine treatment and/or hydrogen treatment, as would be familiar to the skilled artisan, as part of the activation process.

For the purposes of this description, all parts per million figures are on a weight to volume basis, i.e., grams/million cubic centimeters (which can also be expressed as milligrams/liter), and percentages are given by weight, unless otherwise indicated. Although for the sake of convenience this description will be written in terms of a reforming reactor, it will be understood that the present invention is applicable to any catalytically-mediated hydroprocessing reactor.

Feedstocks commonly used in a hydroprocessing reactor are hydrocarbon streams, most often made up of alkanes and aromatics (i.e., C-4 through C-30) depending on the reaction(s) desired, which are passed over the catalyst under hydrogen pressures which can range from about 0 to about 3000 pounds per square inch (psi), and at temperatures ranging from about 200° C. to about 570°C., although wide variations in pressure and temperature are possible depending on the particular feedstock, the particular reforming reactor, the particular catalyst used and other process parameters. The feedstock also contains a hydrogen stream to assist in the desired reaction.

The catalysts used in such reactors are chosen with respect to the particular reaction(s) desired and are generally platinum group metals, especially platinum itself, coated on a catalyst bed or base such as alumina, silica or chlorinated alumina and/or zeolite mordenite or other zeolites (although other suitable catalyst bases will be familiar to the skilled artisan). Manufacture of such catalysts is well within the skill of the practitioner.

The method of the present invention comprises admixing with the feedstock, hydrogen stream or recycle stream (which is a stream of recycled feedstock after contact with the catalyst) of a reforming reactor an additive which comprises a nonionic, organometallic platinum group metal coordination composition. The composition should be temperature stable and should not contain a substantial amount of phosphorus, arsenic, sulfur, antimony or halides (although in the case of hydrocracking, halides might be desired to be present). The nonionic, organic nature of the composition provides solubility in the feedstock or recycle stream, thereby facilitating the introduction of the additive to the catalyst to be regenerated. Without such solubility, much of the additive would precipitate in the feedstock or recycle stream lines prior to introduction onto the catalyst to be regenerated.

Temperature stability of the additive of this invention is important in practical and operational terms. In a commercial setting, an additive is often stored for extended periods of time during which it can be exposed to great variations in temperature. If the breakdown temperature of the additive is not sufficiently high (i.e. if the additive is not temperature stable at the temperatures to which it is expected to be exposed), then the additive will quickly break down and become virtually useless. Moreover, breakdown of the additive after mixing with the feedstock or recycle stream will render the additive insoluble, since the solubility is provided by the organic functional groups. Such loss of solubility will cause the additive to precipitate and not reach the catalyst base, as discussed above. Typically, the breakdown temperature of the additive should be at least about 40° C., preferably at least about 50° C. in order to protect against most temperatures to which it can be expected to be exposed. In some circumstances, it will be necessary that the breakdown temperature be no lower than about 75° C.

In addition, the breakdown temperature of the additive should not be so high as to resist breakdown of the additive at the catalyst to be regenerated, or regeneration or redeposit of catalyst metal on the catalyst base will not occur. The breakdown temperature of the additive, therefore, should be no greater than the temperatures of the reformer in the vicinity of the catalyst to be regenerated, i.e., no greater than about 570° F.

In general, the additive comprises the platinum metal group composition as well as a hydrocarbon solvent therefor, as noted above. The nonionic, organic nature of the platinum group metal composition helps to maintain the composition in solution in the solvent, thereby preventing "plating out" of the platinum group metal composition in storage or in the feedstock or recycle stream lines.

As noted, the additive of the present invention should not contain a substantial amount of objectionable functional groups such as phosphorus, arsenic, sulfur, antimony and halides, which have disadvantages like "poisoning" or otherwise reducing the catalytic effectiveness of the platinum group metal composition. Halides have the additional undesirable effect of rendering a platinum group metal more volatile, leading to reduction of the amount of platinum group metal which remains deposited on the catalyst base. A substantial amount of such functional groups is considered an amount effective to significantly reduce the effectiveness of the catalyst. Preferably, the purified platinum group metal additive composition contains no more than about 500 ppm (on a weight of functional groups per weight of platinum group metal basis) of phosphorus, arsenic, antimony or halides, more preferably no more than about 250 ppm.

Such objectionable functional groups can be minimized in several ways. The platinum group metal composition can be prepared in a process which utilizes precursors or reactant compositions having a minimum of such functional groups; or the additive can be purified after preparation. Most such methods of purification are known to the skilled artisan.

One preferred method of purifying the platinum group metal additive to remove halides is a process utilizing silver salts having non-halide anions which are harmless as compared to the halides being replaced and involves reacting them with the platinum group metal compound, whereby the halides in the composition are replaced by the anion of the silver salt (which can be any silver salts of carboxylic acids, such as silver benzoate) and the resulting composition is free of halides, plus a silver halide is produced. For instance, a slurry or solution in a polar solvent such as acetone or an alcohol and water of silver benzoate can be prepared and reacted with the platinum group metal composition. The resultant platinum group metal composition is a benzoate salt with silver halide also being produced. This process can be expected to reduce the halide content of a sample by about 50%, and even up to about 90% and higher.

Platinum group metals include platinum, palladium, rhodium, ruthenium, osmium and iridium. Compounds including platinum, palladium and rhodium, especially platinum alone or possibly in combination with rhodium are preferred in the practice of this invention since they are efficient at catalyzing the desired reactions.

Specific suitable compounds according the present invention include those platinum metal group-containing compositions selected from the group consisting of a) a composition of the general formula $$L^1 Pt R^1 R^2$$

wherein $L^1$ is either a single cyclic polyolefin or nitrogenous bidentate ligand or a pair of nitrogenous or acetylenic monodentate ligands; and $R^1$ and $R^2$ are each, independently, substituted or unsubstituted methyl, benzyl, aryl, cyclopentadiene or pentamethyl cyclopentadiene, preferably benzyl, methyl and/or phenyl;

b) a composition of the general formula $$L^2 M^1 R^3$$

wherein $L^2$ is either a single cyclic polyolefin or nitrogenous bidentate ligand or a pair of nitrogenous or acetylenic monodentate ligands; $M^1$ is rhodium or iridium; and $R^3$ is cyclopentadiene or pentamethyl cyclopentadiene;

c) a composition of the general formula $$L^3 M^2 (C_4 R^4_4)$$

wherein $L^3$ is either a single cyclic polyolefin or nitrogenous bidentate ligand or a pair of nitrogenous monodentate ligands; $M^2$ is platinum, palladium, rhodium or iridium; and $R^4$ is $COOR^5$, wherein $R^5$ is hydrogen or alkyl having from 1 to 10 carbons, preferably methyl;

d) a composition of the general formula $$L^4 M^3 (COOR^6)_2$$

or a dimer thereof, wherein $L^4$ is a non-nitrogenous cyclic polyolefin ligand, preferably cyclooctadiene or pentamethyl cyclopentadiene; $M^3$ is platinum or iridium; and $R^6$ is benzyl, aryl or alkyl, preferably having 4 or more carbons, most preferably phenyl;

e) a composition comprising the reaction product of $[L^5 RhX]_2$ and $R^7 MgX$ wherein $L^5$ is a non-nitrogenous cyclic polyolefin ligand, preferably cyclooctadiene or pentamethyl cyclopentadiene; $R^7$ is methyl, benzyl, aryl, cyclopentadiene or pentamethyl cyclopentadiene, preferably benzyl or phenyl; and X is a halide. Although presently uncharacterized, it is believed that this reaction product assumes the formula $L^5 RhR^7$.

Functional groups which are especially preferred for use as ligands $L^1$ through $L^3$ are neutral bidentate ligands such as cyclopentadiene, cyclooctadiene, pentamethyl cyclopentadiene, cyclooctatetrene, norbornadiene, o-toluidine, o-phenantholine and bipyridine. Preferred among monodentate ligands is pyridine.

Functional groups which do not contain nitrogen are considered more desirable than those which contain nitrogen. This is because nitrogenous functional groups may lead to the presence of nitrogen, especially in the form of nitrates, in the reactor, which are considered disadvantageous.

The synthesis of the preferred compounds is relatively straightforward, with the most care being taken to avoid "contamination" of the product by the objectionable functional groups discussed above. For instance, the most preferred synthetic route for production of the compounds of the formula $L^1 PtR^1 R^2$ is by reacting commercially available platinum halides with the desired neutral ligand (except the pyridine derivative which can be added by displacement after the fact) and then reacting with a Grignard reagent having the formula $R_2 MgX$, where X is a halide (and where the desired $R^1$ and $R^2$ in the end product are the same functional group). Where the $R^1$ and $R^2$ functional groups are desired to be different, a straightforward substitution reaction can then be run. Exemplary of compounds suitable for use in the present invention and prepared in this manner are dipyridine platinum dibenzyl; bipyridine platinum dibenzyl; cyclooctadiene platinum dimethyl; cyclooctadiene platinum diphenyl; cyclooctadiene platinum dibenzyl; cyclooctadiene platinum methyl cyclopentadiene; norbornadiene platinum di-cyclopentadiene; and dimethyl platinum cyclooctatetrene (which often assumes the formula dimethyl platinum cyclooctatetrene platinum dimethyl).

The compounds of the formula $L^2 M^1 R^3$ are prepared along a similar pathway, as are the reaction products of $[L^5 RhX]_2$ and $R^6 MgX$, with the exception that the starting materials have only one R functional group and are, with respect to $L^2 M^1 R^3$, $L^2 RhR^3$ or $L^2 IrR^3$. Exemplary of suitable compounds of the formula $L^2 M^1 R^3$ are cyclooctadiene rhodium cyclopentadiene; cyclooctadiene rhodium pentamethyl cyclopentadiene; norbornadiene rhodium pentamethyl cyclopentadiene; cyclooctadiene iridium cyclopentadiene; cyclooctadiene iridium pentamethyl cyclopentadiene; norbornadiene iridium cyclopentadiene; and norbornadiene iridium pentamethyl cyclopentadiene. Exemplary of compounds which can function as the precursors for the reaction product can include cyclooctadiene rhodium chloride dimer and benzyl magnesium chloride.

Advantageously, in the Grignard-type syntheses, the Grignard reagent can be replaced by one having the formula RZ where Z is commonly Na, Li, K or Tl. This is especially preferred since the halides which are present in a Grignard reagent are eliminated, providing less halides in the final product and also advantageously producing a higher yield of the desired product.

The preparation of compositions of the formula $L^3M^2(C_4R^4_4)$ is also straightforward and proceeds by reacting $M^2$(dibenyilidine acetone)$_2$ with dimethylacetylene dicarboxylate in acetone and then adding the $L^3$ ligand. Exemplary of suitable compounds according to this formula, which has the structure

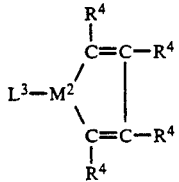

is cyclooctadiene tetrakis (methoxy carbonyl) palladia cyclopentadiene (wherein $L^3$ is cyclooctadiene, $M^2$ is palladium, and $R^4$ is COOCH$_3$).

The compositions of the formula $L^4M^3(COOR^5)_2$ can be prepared by reacting $L^4M^3X_2$, where X is a halide and a silver carboxylate such as silver benzoate. This composition can form a dimer, especially when $M^3$ is platinum. Exemplary of suitable compounds having the general formula $L^4M^3(COOR^5)_2$ are cyclooctadiene platinum dibenzoate dimer; and pentamethyl cyclopentadiene iridium dibenzoate.

The additive will be added or blended or admixed into the feedstock or recycle stream by known means in an amount effective to improve catalytic activity. Suitable amounts for the most preferred intermittent method of application of the additive of this invention to the feedstock or the recycle stream and for the continuous method of application are those discussed above.

As noted, the additive composition will preferably include a solvent which is soluble in the feedstock or recycle stream, preferably a carrier such as kerosene, xylene or other hydrocarbons and possibly also with certain other solvents which provide enhancements in the effectiveness of the platinum group metal compound. Other suitable solvents are oxygenated hydrocarbons, such as alcohols, heterocyclic oxygen compounds and ethers, although the use of oxygenates may be undesirable when the continuous method of operation is employed due to the tendency of them to react with the hydrogen to form water. Particular oxygenates are: 1 to 4 carbon alcohols, especially ethanol; acetone; tetrahydrofuran and methyl tertiary butyl ether.

The inventive additive can also be added to the hydrogen stream of the reforming reactor. When the method of the present invention involves the application of the additive to the hydrogen stream, the additive is introduced into the stream such as by spraying using conventional injectors or other suitable injection means at a rate of about 0.000002 to about 0.002 grams of platinum group metal per hour per 100 grams of catalyst desired to be present, in order to produce continuous catalyst regeneration or redeposit effect. To produce intermittent catalyst regeneration or redeposit, the additive should be supplied at a rate of about 0.002 to about 2.0 grams of platinum group metal per hour per 100 grams of catalyst desired to be present.

By the practice of the present invention, the platinum group metal composition which is present in the feedstock, recycle stream or hydrogen stream comes into contact with the catalyst. Upon such contact with the platinum group metal composition, the platinum group metal is caused to be deposited on the catalyst, providing active catalyst. This can be considered, in effect, equivalent to regenerating, replacing or treating the catalyst without the need for disassembly of the reactor or other undesirable and economically disadvantageous procedures.

Besides the direct benefit achieved by the present invention, the redeposit or regeneration of catalyst without disassembly of the reformer, an additional advantageous effect is in the ability to expand the available feedstock to include a higher fraction of less desirable materials since the catalytic effect is maintained at a high level. In addition, the intimate mixture of additive with the less desirable feedstock improves the catalytic efficiency of the system. This can result in a significant improvement in process economics, beside the economic improvements gained by eliminating the need to disassemble the reforming reactor to perform catalyst regeneration, replacement or treatment.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

We claim:

1. A method for regenerating, replacing or treating the catalyst in a hydroprocessing reactor, which catalyst comprises a platinum group metal on a support, the method comprising admixing with the feedstock, recycle stream or hydrogen stream of the reactor an additive which comprises a nonionic, organometallic platinum group metal coordination composition wherein said composition
   a) has a breakdown temperature between about 40° C. and about 570° C.; and
   b) is substantially free from a disadvantageous amount of phosphorus, arsenic, sulfur, antimony or halides, wherein platinum group metal is caused to be deposited on said catalyst.

2. The method of claim 1 wherein said composition is selected from the group consisting of
   a) a composition of the general formula

wherein $L^1$ is either a single cyclic polyolefin or nitrogenous bidentate ligand or a pair of nitrogenous or acetylenic monodentate ligands; and $R^1$ and $R^2$ are each, independently, substituted or unsubstituted methyl, benzyl, aryl, cyclooctadiene or pentamethyl cyclopentadiene;

b) a composition of the general formula $$L^2M^1R^3$$

wherein $L^2$ is either a single cyclic polyolefin or nitrogenous bidentate ligand or a pair of nitrogenous or acetylenic monodentate ligands; $M^1$ is rhodium or iridium; and $R^3$ is cyclopentadiene or pentamethyl cyclopentadiene;

c) a composition of the general formula $$L^3M^2(C_4R^4{}_4)$$

wherein $L^3$ is either a single cyclic polyolefin or nitrogenous bidentate ligand or a pair of nitrogenous monodentate ligands; $M^2$ is platinum, palladium, rhodium or iridium; and $R^4$ is $COOR^5$, wherein $R^5$ is hydrogen or alkyl having from 1 to 10 carbons;

d) a composition of the general formula $$L^4M^3(COOR^6)_2$$

or a dimer thereof, wherein $L^4$ is a non-nitrogenous cyclic polyolefin ligand; $M^3$ is platinum or iridium; and $R^6$ is alkyl; and e) a composition comprising the reaction product of $L^5RhX$ and $R^7MgX$ wherein $L^5$ is a non-nitrogenous cyclic polyolefin ligand; $R^7$ is methyl, benzyl, aryl, cyclopentadiene or pentamethyl cyclopentadiene; and X is a halide.

3. The method of claim 2 wherein $L^1$, $L^2$ and $L^3$ are selected from the group consisting of cyclopentadiene, cyclooctadiene, pentamethyl cyclopentadiene, cyclooctatetrene, o-phenantholine, o-toluidine, norbornadiene, pyridine and bipyridine.

4. The method of claim 2 wherein $L^4$ and $L^5$ are selected from the group consisting of cyclooctadiene and pentamethyl cyclopentadiene.

5. The method of claim 4 wherein said additive further comprises a feedstock- or recycle stream-soluble solvent for said composition.

6. The method of claim 5 wherein said solvent is selected from the group consisting of 1 to 4 carbon alcohols, acetone, tetrahydrofuran, methyl tertiary butyl ether and mixtures thereof.

7. The method of claim 1 wherein said additive is introduced into the feedstock, the recycle stream or the hydrogen stream in a continuous manner.

8. The method of claim 7 wherein said additive is introduced into the feedstock or the recycle stream in an amount of about 0.01 to about 10.0 parts per million of said platinum group metal.

9. The process of claim 7 wherein said additive is introduced into the hydrogen stream at a rate of about 0.000002 to about 0.002 grams of platinum group metal per hour per 100 grams of catalyst desired to be present.

10. The method of claim 1 wherein said additive is introduced into the feedstock, the recycle stream or the hydrogen stream in an intermittent manner.

11. The method of claim 10 wherein said additive is introduced into the feedstock or recycle stream in an amount of about 10 to about 10,000 parts per million of said platinum group metal.

12. The process of claim 10 wherein said additive is introduced into the hydrogen stream at a rate of about 0.002 to about 2.0 grams of platinum group metal per hour per 100 grams of catalyst desired to be present.

13. A method for regenerating, replacing or treating the catalyst in a hydroprocessing reactor, which catalyst comprises a platinum group metal on a support, the method comprising intermittently admixing with the feedstock or recycle stream of the reactor an additive which comprises a nonionic, organometallic platinum group metal coordination composition at a temperature of below about 200° C. wherein said composition a) has a breakdown temperature between about 40° and about 570° C.; and b) is substantially free from a disadvantageous amount of phosphorus, arsenic, antimony. or halides, wherein platinum group metal is caused to be deposited on said catalyst.

14. The method of claim 13 wherein said composition is selected from the group consisting of a) a composition of the general formula $$L^1PtR^1R^2$$

wherein $L^1$ is either a single cyclic polyolefin or nitrogenous bidentate ligand or a pair of nitrogenous or acetylenic monodentate ligands; and $R^1$ and $R^2$ are each, independently, substituted or unsubstituted methyl, benzyl, aryl, cyclooctadiene or pentamethyl cyclopentadiene;

b) a composition of the general formula $$L^2M^1R^3$$

wherein $L^2$ is either a single cyclic polyolefin or nitrogenous bidentate ligand or a pair of nitrogenous or acetylenic monodentate ligands; $M^1$ is rhodium or iridium; and $R^3$ is cyclopentadiene or pentamethyl cyclopentadiene;

c) a composition of the general formula $$L^3M^2(C_4R^4{}_4)$$

wherein $L^3$ is either a single cyclic polyolefin or nitrogenous bidentate ligand or a pair of nitrogenous monodentate ligands; $M^2$ is platinum, palladium, rhodium or iridium; and $R^4$ is $COOR^5$, wherein $R^5$ is hydrogen or alkyl having from 1 to 10 carbons;

d) a composition of the general formula $$L^4M^3(COOR^6)_2$$

or a dimer thereof, wherein $L^4$ is a non-nitrogenous cyclic polyolefin ligand; $M^3$ is platinum or iridium; and $R^6$ is alkyl; and e) a composition comprising the reaction product of $L^5RhX$ and $R^7MgX$ wherein $L^5$ is a non-nitrogenous cyclic polyolefin ligand; $R^7$ is methyl, benzyl, aryl, cyclopentadiene or pentamethyl cyclopentadiene; and X is a halide.

15. The method of claim 14 wherein $L^1$, $L^2$ and $L^3$ are selected from the group consisting of cyclopentadiene, cyclooctadiene, pentamethyl cyclopentadiene, cyclooctatetrene, o-phenantholine, o-toluidine, norbornadiene, pyridine and bipyridine.

16. The method of claim 14 wherein $L^4$ and $L^5$ are selected from the group consisting of cyclooctadiene and pentamethyl cyclopentadiene.

17. The method of claim 14 wherein said additive further comprises a feedstock- or recycle stream-soluble solvent for said composition.

18. The method of claim 17 wherein said solvent is selected from the group consisting of 1 to 4 carbon alcohols, acetone, tetrahydrofuran, methyl tertiary butyl ether and mixtures thereof.

19. The method of claim 13 wherein said additive is introduced into the feedstock or recycle stream in an amount of about 10 to about 10,000 parts per million of platinum group metal.

* * * * *